(12) United States Patent
Vagle et al.

(10) Patent No.: US 7,276,598 B2
(45) Date of Patent: Oct. 2, 2007

(54) PHOSPHORYLATION REAGENTS FOR IMPROVED PROCESSES TO CONVERT TERMINAL HYDROXYL GROUPS OF OLIGONUCLEOTIDES INTO PHOSPHATE MONOESTERS

(75) Inventors: Kurt Vagle, Longmont, CO (US); Michael Leuck, Hamburg (DE); Andreas Wolter, Hamburg (DE)

(73) Assignee: Sigma-Aldrich Co., St. Louis, MO (US)

( * ) Notice: Subject to any disclaimer, the term of this patent is extended or adjusted under 35 U.S.C. 154(b) by 490 days.

(21) Appl. No.: 10/821,631

(22) Filed: Apr. 9, 2004

(65) Prior Publication Data

US 2004/0230047 A1    Nov. 18, 2004

Related U.S. Application Data

(60) Provisional application No. 60/461,730, filed on Apr. 9, 2003.

(51) Int. Cl.
*C07H 5/06* (2006.01)
*C07H 21/04* (2006.01)

(52) U.S. Cl. ................... 536/25.3; 536/25.31
(58) Field of Classification Search ............... 536/25.3, 536/25.31
See application file for complete search history.

(56) References Cited

U.S. PATENT DOCUMENTS 5,252,760 A    10/1993   Urdea et al.
5,959,090 A     9/1999   Guzaev et al.

OTHER PUBLICATIONS

Connolly (1987) Tetrahedron Letters 28:463-466.
Guzaev et al. (1995) Tetrahedron 51:9375-9384.
Guzaev et al. (1999) Tetrahedron 55:9101-9116.
Guzaev et al. (2001) Tetrahedron Letters 42:4769-4773.
Horn and Urdea (1986) Tetrahedron Letters 27:4705-4708.
Schwarz and Pfleiderer (1987) Nucleosides & Nucleotides 6:537-539.
Uhlmann and Engels (1986) Tetrahedron Letters 27:1023-1026.

*Primary Examiner*—Shaojia Anna Jiang
*Assistant Examiner*—Ganapathy Krishnan
(74) *Attorney, Agent, or Firm*—Jeffrey A. Wilson

(57) ABSTRACT

The present invention discloses novel phosphoramidite reagents for use in oligonucleotide synthesis. The present invention further discloses novel methods for the conversion of terminal hydroxyl groups of oligonucleotides into phosphate monoesters. By employing novel reagents, as also disclosed herein, the methods are fully compatible with standard procedures for solid phase oligonucleotide synthesis and do not require additional processing steps. The inventive reagents to phosphorylate terminal hydroxyl groups of oligonucleotides are superior to the prior art in that they for the first time combine the desired attributes of being a solid compound for facile handling, comprising two β-eliminating protective groups removable as fast or faster than the standard cyanoethyl group, providing a DMT-group for easy monitoring of the coupling efficiency, and enabling a fast final deprotection of the phosphorylated oligonucleotide without any extra manipulation steps.

1 Claim, 2 Drawing Sheets

PHOSPHORYLATION REAGENTS FOR IMPROVED PROCESSES TO CONVERT TERMINAL HYDROXYL GROUPS OF OLIGONUCLEOTIDES INTO PHOSPHATE MONOESTERS

FIELD OF THE INVENTION

The present invention relates to the field of nucleotide chemistry. More specifically, the invention relates to the field of oligonucleotide synthesis including the chemical modification of oligonucleotides.

BACKGROUND OF THE INVENTION

The enormous increase in demand for synthetic oligonucleotides, fueled by the advances in DNA technology over the last decades, has been accelerated by recent progress in sequencing and decoding whole genomes, particularly the human genome. A number of methods in molecular biology and DNA based diagnostics to amplify, detect, analyze and quantify nucleic acids are dependent on chemically synthesized oligonucleotides.

Some applications of synthetic oligonucleotides in molecular biology require the presence of a terminal phosphate moiety, which is introduced into the synthetic oligonucleotides using specially designed phosphorylation reagents. One major application of synthetic oligonucleotides with terminal 5'-phosphate moieties is the enzymatic ligation of the oligonucleotide to another oligonucleotide with a 3'-OH group. Ligation reactions take place when the terminal 5'-phosphate of one oligonucleotide annealed to a template DNA strand is joined to a 3'-hydroxyl group of a second strand of annealed oligonucleotide adjacent to the first by a ligase enzyme. Terminal 5'-phosphate moieties are also amenable to the ligase chain reaction, which is useful to determine the sequence of a DNA sample, to detect certain types of DNA or to detect single point mutations in disease genes. Terminal 5'-phosphates are also useful to those skilled in the art for the purpose of building longer oligonucleotides for molecular cloning and gene construction. Terminal phosphate groups are also known by those skilled in the art to be amenable to covalent attachment via standard dehydration reactions with reporter groups bearing alcoholic substituents. Finally, terminal phosphate groups improve the stability of synthetic oligonucleotides by reducing exonucleolytic degradation.

The current state of the art in oligonucleotide synthesis is automated solid phase synthesis using phosphoramidite chemistry, which, in particular, is based on the developments of McBride et al. (1983) Tetrahedron Letters 24:245-248 and Sinha et al. (1983) Tetrahedron Letters 24:5843-5846, each of which is incorporated herein by reference in its entirety. Phosphoramidite chemistry, together with related methods such as hydrogen phosphonate chemistry, has been extensively reviewed with respect to their uses in oligonucleotide chemistry by Beaucage et al. (1992) Tetrahedron 48:2223-2311, which is incorporated herein by reference in its entirety. During solid phase oligonucleotide synthesis, a series of nucleotide monomers are sequentially attached, via their phosphoramidite derivatives, in a predetermined order to either, depending on the direction of chain extension, the 5'-functional group or the 3'-functional group of the growing oligonucleotide strand. The oligonucleotide strand is anchored to an insoluble moiety such as controlled pore glass or polystyrene resin beads. The method of attachment of each monomer is generally comprised of the following steps:

1. Deprotection of the reactive functionality. The common reactive functionality is the 5'-hydroxyl group of the terminal nucleoside. This functionality is usually protected with a 4,4'-dimethoxytrityl (DMT) moiety that can be removed via acid treatment. One of the attractive features of the DMT moiety is that it forms a bright orange DMT cation during acid deprotection. This cation serves effectively as reporter group that can be easily monitored at a wavelength between 480 and 500 nm for the purpose of judging the completeness the previous coupling step. Most commercially available automated synthesizers have the capability to monitor the released DMT cation. This data gives the operator an instant indication of whether or not the synthesis failed at any given step.
2. Coupling by addition of a phosphoramidite derivative and an activator. The phosphoramidite derivative is usually a nucleoside phosphoramidite, however, it may also be a phosphoramidite derivatized with a different organic moiety.
3. Capping of unreacted terminal functional groups. This step introduces an inert protective group that prevents further coupling to failure sequences.
4. Oxidation of the newly formed phosphorous nucleotide backbone linkage from the trivalent phosphite to the stable pentavalent phosphate state.
5. After a washing step, the process is repeated.

The current state of the art in the introduction of terminal 5'-O-phosphate groups into synthetic oligonucleotides relies on phosphoramidite reagents that are employed in the final coupling cycle of the oligonucleotide synthesis. The preferred phosphoramidite reagents carry two phosphate protective groups that are removed via mild basic hydrolysis. In most variants of such phosphoramidite reagents one of the protective groups is a cyanoethyl group, an industry standard phosphate protective group when oligonucleotides are produced using phosphoramidite chemistry. The cyanoethyl protective group is removed under mild basic conditions after oxidation to the pentavalent phosphate species and is stable to the strongly acidic conditions employed in the deprotection step of oligonucleotide synthesis cycles. Cyanoethyl protective groups are removed concurrently by the final ammonium hydroxide treatment that is required to cleave the linkage of the oligonucleotide to the solid support. In commercially available phosphoramidite reagents for the introduction of terminal phosphate moieties the second protective group is also susceptible to base hydrolysis and contains a reporter group, usually a DMT group that can be removed by acid treatment. The significance of the DMT group is due to the common practice of monitoring amidite coupling efficiencies by measuring the release of the colored DMT cation from the previously coupled phosphoramidite derivative. The DMT cation is easily monitored by VIS-spectroscopy at a wavelength between 480 and 500 nm.

Cyanoethyl protective groups belong to a class of phosphate protective groups known as "β-eliminators." β-Eliminators are phosphate protective groups that are removable with aqueous bases such as ammonium hydroxide. β-Eliminators are cleaved by a mechanism that does not involve the attack of a cleavage reagent at the phosphorus center. Therefore, phosphates protected with β-eliminating protective groups are not amenable to side reactions such as chain cleavage reactions, which is a known problem with phosphate protective groups that are cleaved by other mechanisms. Thus, most of the phosphate protective groups used in oligonucleotide synthesis are β-eliminators. Until now, however, there have been no examples of dual cyanoethyl-protected phosphoramidites that incorporate a reporter group. Additionally, there are no examples of β-eliminating phosphate protective groups that are functionalized at the alpha position.

The second protective group in the state of the art phosphoramidite reagents for the introduction of terminal phosphate groups can be either a different β-eliminating protective group or a protective group that requires additional manipulations before it is released. Either type of protective group also incorporates an ether linkage to a DMT group which, when cleaved by acid, serves as a reporter group. Horn et al., U.S. Pat. No. 5,252,760 and (1986) Tetrahedron Letters 27:4705-4708, each of which is specifically incorporated herein by reference in its entirety, have described the use of a state of the art chemical phosphorylation reagent that has one cyanoethyl group and a unique second β-eliminating group that contains a DMT reporter group and can be removed via mild basic hydrolysis. This phosphorylation reagent, however is a hard to handle viscous oil. This drawback is especially manifest due to the fact that very small amounts of reagent are required to be packaged in amber bottles when using current state of the art automated oligonucleotide synthesis. This makes assessment of whether or not the compound is fully dissolved very difficult.

Guzaev et al., U.S. Pat. No. 5,959,090, (1995) Tetrahedron 51:9375-9384 and (1999) Tetrahedron 55:9101-9116, each of which is specifically incorporated herein by reference in its entirety, have described the use of another state of the art phosphoramidite reagent for the introduction of terminal phosphate groups that carries one cyanoethyl group and a unique phosphate protective group containing the desired DMT reporter group. However, this phosphoramidite reagent requires two manipulations to be fully deprotected. The mechanism of deprotection requires that the DMT group be removed via acid treatment followed by mild basic treatment that leads to a retrograde aldol reaction followed by a β-elimination. It should be noted that complete detritylation must be realized using this reagent, otherwise, significant impurities will be present in the final product due to the partially protected terminal phosphate. Experimental results reported by the Guzaev et al. show that detritylation conditions must be stringent in order to ensure complete detritylation. At least two detritylation cycles on an automated oligonucleotide synthesizer must be employed when using this reagent. This can lead to further complexity in modern, high-throughput, automated oligonucleotide synthesizers as well as additional oligonucleotide impurities that are known to occur upon prolonged treatment with acid. It should also be noted that this reagent in its diester form is a viscous oil that suffers from the same problems noted for the Horn et al. reagent. This reagent in its bis(ethylamido) form is a solid, however, it suffers from the same deprotection issues as the diester form as well as requiring an inconvenient and long synthesis procedure. Recently, Guzaev et al. (2001) Tetrahedron Lett. 42:4769-4773, which is specifically incorporated herein by reference in its entirety, have disclosed an improvement to the aforementioned reagents by introducing a TMT (trimethoxytrityl) group instead of the formerly employed DMT-group. The TMT-group is more easily removed than the DMT-group under acidic conditions, but it is also less convenient for monitoring coupling efficiencies, because the spectral characteristics of the released TMT-cation differ from those of the DMT-cation.

A phosphoramidite reagent for the routine synthesis of oligonucleotides with terminal phosphate moieties should fulfill the following criteria:
A) It should contain a reporter group, preferably a DMT-group, that can be monitored calorimetrically at a wavelength between 480 and 500 nm;
B) It should contain two β-eliminating phosphate protective groups;
C) It should not require additional manipulations to effect final deprotection after the reagent is added to the oligonucleotide in the standard synthesis cycle; and
D) It should be a solid that can be easily manipulated by an operator and can be easily monitored with respect to whether or not the reagent is completely solubilized.

Until now, there is no one reagent that meets all of the aforementioned criteria. The commercialized state of the art phosphoramidite reagent described by Horn et al. is a viscous oil that is difficult to monitor when dissolving. The reagent described by Guzaev et al. is also a viscous oil that requires additional manipulations to effect final deprotection. The bis(ethylamido)-derivative described by Guzaev et al. is a solid, however, it still requires additional manipulations to effect the final deprotection that yields the terminal 5'-O-phosphate monoester.

A variety of other phosphoramidite reagents for the introduction of terminal phosphate moieties in the last coupling cycle of an oligonucleotide synthesis have been described in the scientific literature. Examples include reagents with two allyl phosphate protective groups as described by Bannwarth et al. (1989) Tetrahedron Letters 30:4219-4222, a reagent with a methyl phosphate protective group and a tritylthioethyl phosphate protective group as described by Connolly (1987) Tetrahedron Letters 28:463-466, reagents with two 2-cyanoethyl phosphate protective groups or two p-nitrophenylethyl phosphate protective groups as described by Uhlmann et al. (1986) Tetrahedron Letters 27:1023-1026, and another reagent with two p-nitrophenylethyl phosphate protective groups as described by Schwarz et al. (1987) Nucleosides & Nucleotides 6:537-539. A comprehensive review of the field is described by Beaucage et al. (1993) Tetrahedron 49:10441-10488. Each of the references cited above is specifically incorporated herein by reference in its entirety.

None of the phosphoramidite reagents described in these references fulfills all of the criteria set forth above. None of the described reagents contain a reporter group useful for monitoring the efficiency of the coupling reaction of the reagent. In addition, they are viscous liquids which are difficult to place into vials or bottles and which are hard to visually monitor for complete dissolution in the solvent of the coupling reaction. Also, some of the reagents require an additional manipulation step in the deprotection of the synthetic oligonucleotide. For example, the p-nitrophenylethyl phosphate protective group requires treatment with the strong base DBU in addition to the standard ammonia treatment in order to achieve its complete removal. Another example is the tritylthioethyl group, which requires the removal of the trityl group from the sulfur atom with silver salts in addition to the standard ammonia treatment. Additionally, some of the described reagents contain phosphate protective groups that are cleaved through an attack of a deprotecting agent at the phosphorus atom, a mechanism that may result in dephosphorylation as a side reaction. For example, the methyl phosphate protective group employed in some of the described reagents is removed through an attack of strong nucleophiles at the phosphorus atom, which facilitates dephosphorylation as a side reaction.

There is a need for a phosphoramidite reagent that does not suffer from any of the aforementioned disadvantages and that combines all of the favorable features of an ideal phosphoramidite reagent for the introduction of terminal phosphate moieties into synthetic oligonucleotides. The present invention describes novel phosphoramidite reagents that combine all of the criteria set forth above for an ideal phosphoramidite reagent. The phosphoramidite reagents described herein contain a reporter group and comprise two β-eliminating phosphate protective groups, which are removable with ammonia and do not require an additional manipulation step for the deprotection of the synthesized oligonucleotide and that are solid compounds which easily dissolve in the solvent of the phosphoramidite coupling reaction. Included in the present invention are methods for the synthesis of oligonucleotides with terminal phosphate moieties using the phosphoramidite reagents of the invention.

SUMMARY OF THE INVENTION

The present invention discloses novel phosphoramidite reagents for the introduction of terminal phosphate moieties into synthetic oligonucleotides by means of state of the art phosphoramidite chemistry. The reagents are superior to the prior art in that they offer, for the first time, the combination of the following desired characteristics: a) containing a reporter group; b) carrying two β-eliminating protective groups; c) requiring no additional manipulations to effect deprotection; and d) being an easily manipulated solid reagent. The novel phosphoramidite reagents of this invention contain a first β-eliminating phosphate protective group and a second β-eliminating phosphate protective group, wherein said second β-eliminating phosphate protective group is substituted in its α-position. The substituent on the α-position of the second β-eliminating phosphate protective group is comprised of a nucleosidic moiety with a reporter group, wherein said nucleosidic moiety imparts the characteristic of solidity to the reagent. In a preferred embodiment of the invention, the first phosphate protective group is a β-cyanoethyl group and the second phosphate protective group is a β-cyanoethyl group having a substituent in the α-position that contains an O-5'-DMT-thymidin-3'-yl moiety. In a particularly preferred embodiment, the phosphoramidite reagent of the invention is compound (2).

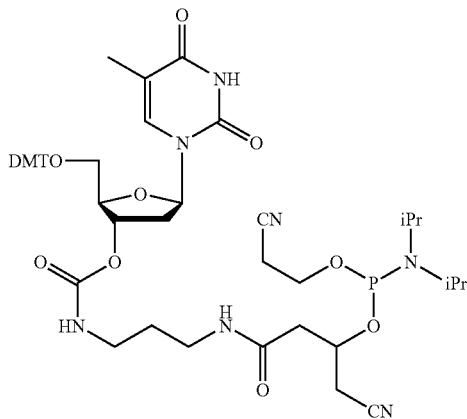

wherein
DMT is a 4,4'-dimethoxytrityl group; and
iPr is an isopropyl group.

The present invention also discloses methods for the preparation of oligonucleotides with terminal phosphate moieties. The methods comprise the coupling of the novel phosphoramidite reagents of this invention with terminal hydroxyl groups of oligonucleotides and the complete removal of the phosphate protective groups of the reagents to provide oligonucleotides with a terminal phosphate monoester. The coupling reaction using the novel reagents of this invention is fast and high yielding. It can optionally be monitored through the release of the reporter group of the reagent. The removal of the phosphate protective groups can be conducted simultaneously with the removal of base protective groups under alkaline conditions without any need for extra chemical steps or additional manipulations. The methods of the invention can be applied to the synthesis of oligonucleotides with either 5'-phosphate moieties, for cases in which the solid phase synthesis of the oligonucleotide is conducted in 3'→5'-direction, or with 3'-phosphate moieties, for cases in which the solid phase synthesis of the oligonucleotide is conducted in 5'→3'-direction. The fully deprotected oligonucleotide containing a terminal phosphate moiety may be recovered and isolated by a variety of known techniques including, but not limited to desalting, gel electrophoresis, anion exchange HPLC, reversed phase HPLC, or any other common method known to those skilled in the art for the recovery and isolation of synthetic oligonucleotides after their deprotection. In a preferred embodiment of the invention, the terminal hydroxyl group of an oligonucleotide is coupled with a phosphoramidite reagent that contains a β-cyanoethyl group as the first phosphate protective group and a β-cyanoethyl group with a substituent in the α-position having an O-5'-DMT-thymidin-3'-yl moiety as the second phosphate protective group. In a particularly preferred embodiment, the terminal hydroxyl group of an oligonucleotide is coupled with the phosphoramidite reagent (2).

The novel reagents and methods of the present invention are useful in any field that requires the chemical synthesis of oligonucleotides with terminal phosphate moieties, e.g. cloning, gene construction, ligase reactions, and post synthetic labeling of oligonucleotides.

DETAILED DESCRIPTION OF THE INVENTION

Figure 1:
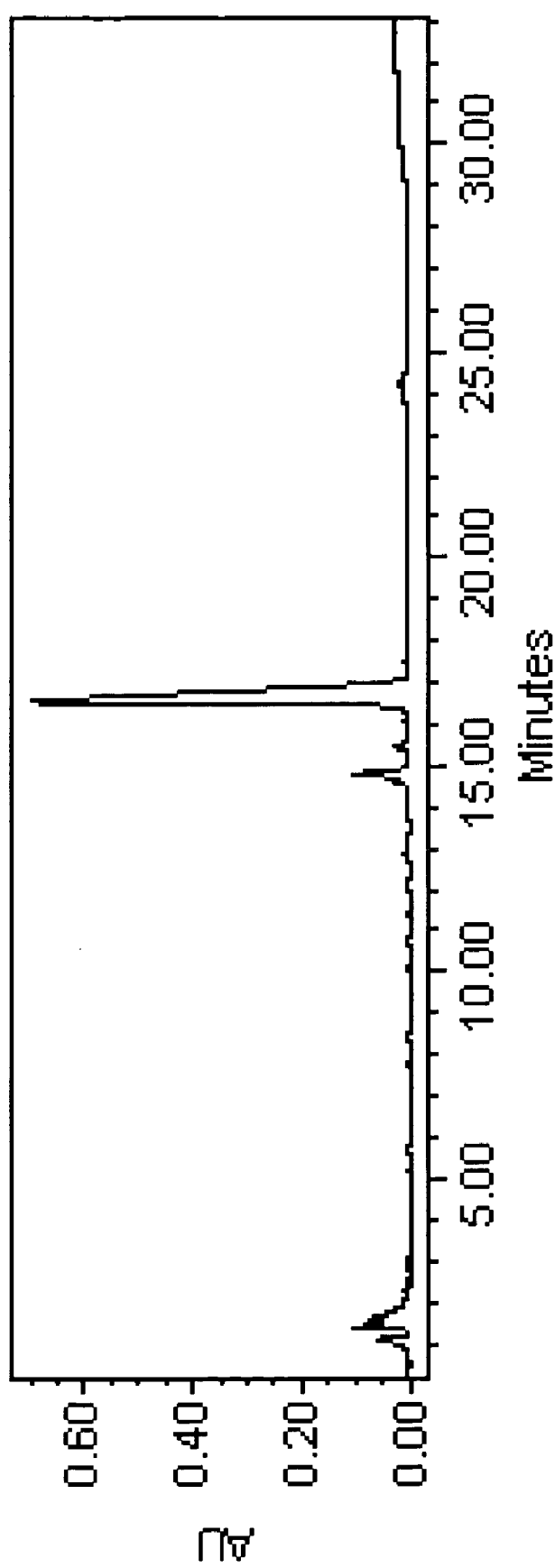
FIG. 1 displays the anion-exchange HPLC chromatogram of the 5'-phosphate oligonucleotide d($T_{10}$) (9) (SEQ ID NO: 1), which was prepared via solid phase synthesis employing phosphoramidite reagent (8) in the last coupling cycle as described in Example 2.
Figure 2:
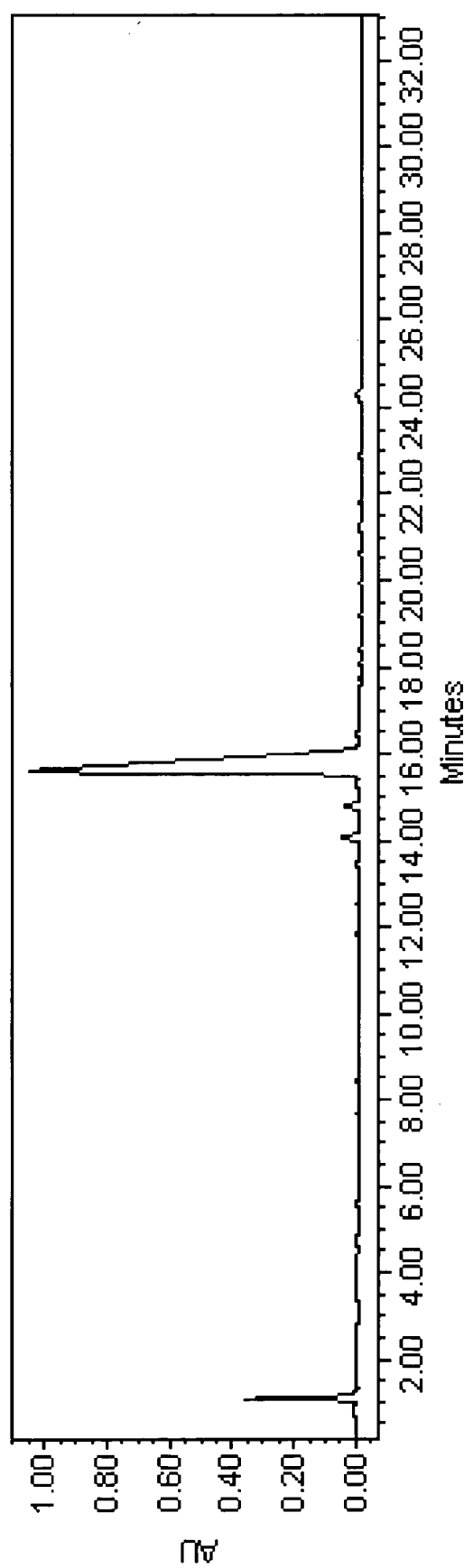
FIG. 2 displays the anion-exchange HPLC chromatogram of the 5'-phosphate oligonucleotide d($T_{10}$) (9) (SEQ ID NO: 1), which was prepared via solid phase synthesis employing phosphoramidite reagent (2) in the last coupling cycle as described in Example 4.

Various terms are used herein to refer to aspects of the present invention. To aid in the clarification of the description of the components of the invention, the following descriptions are provided. It is to be noted that the term "a" or "an" entity refers to one or more of that entity; for example, an oligonucleotide refers to one or more oligonucleotides. As such, the terms "a" or "an," "one or more" and "at least one" are used interchangeably herein.

The phrase "terminal hydroxyl group" as used herein, refers to a hydroxyl group of either the 3'-end nucleotide unit of an oligonucleotide or the 5'-end nucleotide unit of an oligonucleotide, or a hydroxyl group of a spacer or a modifier linked to either the 3'-end nucleotide unit of an oligonucleotide or the 5'-end nucleotide unit of an oligonucleotide. Examples of terminal hydroxyl groups include, but are not limited to the 3'-hydroxyl group of the terminal nucleotide unit, in the case in which the oligonucleotide is synthesized in a 5'→3' direction, or the 5'-hydroxyl group of the terminal nucleotide unit, in the case in which the oligonucleotide synthesis is conducted in a 3'→5' direction.

The term "solid compound" as used herein means a compound which is in a solid state of aggregation at ambient conditions, i.e. at temperatures below 25° C., and which in particular does not have a syrupy, waxy, viscous, or the like appearance. Herein preferred are solid compounds that are crystalline or amorphous solids, or mixtures thereof, capable of being readily processed to a powder.

The term "nucleosidic moiety" as used herein, means a chemical moiety or group that contains either a deoxyribonucleoside or a ribonucleoside or substituted variants thereof or any chemical modifications thereof. The concept of a nucleosidic moiety is described for O5'-DMT-thymidin-3'-yl for purposes of illustration. O5'-DMT-thymidin-3'-yl is a chemical group that contains the O5'-substituted nucleoside thymidine. It may be attached to another group or molecule through the 3'-position of the nucleoside. A nucleosidic moiety may also optionally contain a reporter group, such as a DMT-group, as exemplified by the nucleosidic moiety O5'-DMT-thymidin-3'-yl. A nucleosidic moiety is comprised of any of the common nucleobases including, but not limited to adenine, guanine, cytosine, thymine, uracil, inosine and any other heterocyclic base that may be present in a nucleoside, the nucleobase potentially carrying a base protective group, where appropriate.

As used herein the phrase "base protective group" refers to a protective group useful in oligonucleotide synthesis for protecting exocyclic amino functions of nucleobases or chemical modifications thereof, as exemplified by the benzoyl protective group for adenine and cytosine, the isobutyryl protective group for guanine, tert-butylphenoxyacetyl protective groups for adenine, cytosine and guanine, N,N-dimethylformamidine protective groups for adenine, cytosine and guanine and any other protective groups for nucleobases including any chemical modification thereof, known to those skilled in the art.

As used herein, the term "phosphoramidite reagent" refers to a phosphorous acid diester monoamide compound of the formula P(O——R$_1$)(O—R$_2$)R, which is comprised of a trivalent phosphorous atom bonded to one dialkylamino group (R=NR'R") and two alkoxy groups O—R$_1$ and O—R$_2$, wherein R$_1$ and R$_2$ may be independently selected from phosphate protective groups. In a preferred embodiment, R' and R" are independently selected from an alkyl group having from one to about ten carbons, or R' and R" together form a cyclic alkylene group having from two to up to twenty carbons which may or may not have additional alkyl substituents attached to it and which may contain up to 3 heteroatoms selected from N, O and S included in the cyclic alkylene group. The novel phorphoramidite reagents of this invention are described in more detail below.

The term "phosphate protective group" as used herein refers to chemical moiety that is bonded via an oxygen atom to a tri- or pentavalent phosphorus atom, that is introduced to an oligonucleotide in the course of a solid phase oligonucleotide synthesis to result in a phosphate triester, and that is removable from the oligonucleotide phosphate triester in a selective manner. Examples of phosphate protective groups include, but are not limited to, methyl-, 2-cyanoethyl-, p-nitrophenylethyl-, trichloroethyl-, o-chlorophenyl- and any other phosphate protective group applicable in the context of the synthesis of oligonucleotides. Some phosphate protective groups are susceptible to β-elimination, as defined herein, and have the formula

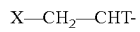

wherein X is an electron-withdrawing moiety and T is H, or a substituent. In one embodiment, X is selected from the group including, but not limited to nitrophenyl, cyano, alkylsulfonyl, or arylsulfonyl, wherein the alkyl moiety is selected from the group including, but not limited to a branched or unbranched alkyl group having from 1 to 10 carbon atoms and the aryl moiety is selected from the group including, but not limited to a phenyl group substituted with 0 to 5 substituents, wherein said substituents are independently selected from the group including, but not limited to chlorine, fluorine, bromine, cyano and nitro.

The term "oligonucleotide synthesis" as used herein refers to any method of solid phase oligonucleotide synthesis (SPOS) known to those of skill in the art. In a preferred embodiment, "oligonucleotide synthesis" includes, but is not limited to either phosphoramidite, phosphotriester and/or nucleoside hydrogen phosphonate chemistries known to those skilled in the art as described e.g. by Gait, ed., "Oligonucleotide synthesis: A practical approach" (1984) IRL Press, Oxford, UK; Eckstein, ed., "Oligonucleotides and analogs: A practical approach" (1991) IRL Press, Oxford, UK; Beaucage et al. (1992) Tetrahedron 48:2223-2311; McBride et al. (1983) Tetrahedron Lett. 24:245-248 and Sinha et al. (1983) Tetrahedron Lett. 24:5843-5846 (1983), each of which is specifically incorporated herein by reference in its entirety, or any other chemistry used in solid phase oligonucleotide synthesis. Typically, oligonucleotide synthesis involves a number of chemical steps that are performed in a cyclical repetitive manner throughout the synthesis with each cycle adding one nucleotide synthon to the growing oligonucleotide chain. The chemical steps involved in a cycle are a deprotection step that liberates a functional group for further chain elongation, a coupling step that incorporates a nucleotide synthon into the oligonucleotide to be synthesized, and other steps as required by the particular chemistry used in the oligonucleotide synthesis, such as e.g. an oxidation step required with the phosphoramidite chemistry. Optionally, a capping step that blocks those functional groups which were not elongated in the coupling step is inserted in the cycle.

The extension of the oligonucleotide chain during the course of an oligonucleotide synthesis is typically pursued in the 3' to 5' direction by adding nucleotide synthons carrying a suitable protective group at the 5'-position, e.g. the widely employed DMT-group (DMT=4,4'-dimethoxytrityl=bis(4-methoxyphenyl)phenylmethyl), and a suitable activatable group, e.g. a phosphoramidite group, at the 3'-position to form a linkage to the 5'-position of the growing chain. The extension of the oligonucleotide chain may alternatively be pursued in the 5' to 3' direction by adding nucleotide synthons in the coupling reaction that carry suitable protective groups at the 3'-position, e.g. a DMT-group, and a suitable activatable group, e.g. a phosphoramidite group, at the 5'-position to form a linkage to the 3'-position of the growing chain. This approach is exemplified in the synthesis of oligodeoxynucleotides with 3'-DMT protected deoxynucleoside 5'-phosphoramidites, as described by e.g. Robles et al. (1995) Nucleic Acids Res. 23:4151-61 (1995), which is specifically incorporated herein by reference in its entirety, or in the synthesis of N3'-P5' phosphoramidite oligonucleotides with N3'-trityl protected nucleoside 5'-phosphoramidites, as described e.g. by Gryaznov et al. (1995) Proc. Nat. Acad. Sci. 92:5798-5802, which is specifically incorporated herein by reference in its entirety.

Nucleotide synthons that are applied in the coupling step of an oligonucleotide synthesis cycle typically are mononucleotide synthons, e.g. the commercially available 5'-DMT protected deoxynucleoside 3'-phosphoramidites, but may be dinucleotide synthons, as described by Kumar et al. (1984) J. Org. Chem. 49:4905-12, which is specifically incorporated herein by reference, or trinucleotide synthons, as described by Ono et al., Nucleic Acids Res. 23, 4677-82 (1995), which is specifically incorporated herein by reference in its entirety, or synthons that consist of more than 3 nucleotide units.

As used herein the term "oligonucleotide" refers to a single stranded chain of either deoxyribonucleotides or ribonucleotides or chemical modifications thereof, such as e.g. nucleotides with a 2'O-4'C-methylene bridge in their sugar portion, which are the constituting nucleotides of locked nucleic acids (LNA). Modifications include, but are not limited to, those that provide other chemical groups that incorporate additional charge, polarizability, hydrogen bonding, electrostatic interaction, and functionality to the individual nucleotides or their corresponding bases or to the oligonucleotides as a whole. Such modifications include, but are not limited to, modified bases such as 2'-position sugar modifications, 5-position pyrimidine modifications, 8-position purine modifications, modifications at cytosine exocyclic amines, substitution of 5-bromo-uracil; backbone modifications, methylations, bases that can be part of unusual base-pairing combinations such as the isobases isocytidine and isoguanidine and the like. Modifications further include attached labels and reporter molecules, such as fluorescent dyes, biotin, minor groove binders and the like that are known to those skilled in the art. In addition modifications include modified backbones of the oligonucleotides, examples being peptide nucleic acids (PNA), phosphorothioate DNA, methylphosphonate DNA and other modifications known to those skilled in the art as reviewed by Micklefield (2001) Current Medicinal Chemistry 8:1157-1179, which is specifically incorporated herein by reference in its entirety. Oligonucleotides, as referred to in this invention can consist of any combinations of the nucleotides and their modifications described above and can have either a few, e.g. up to 20, or many, e.g. 20 to several hundred or more, nucleotides incorporated in their chain.

The term "reporter group" as used herein refers to a protective group which is released during the deprotection step as included in the synthesis cycle of the SPOS, and which provides for measuring the efficiency of the preceding coupling step by measuring the quantity of the released reporter group. Any such group known to those of skill in the art can be used as a reporter group. Photometry and conductivity techniques are preferred examples of methods for determining the quantity of the released reporter group, preferably in a flow-through format. The most preferred reporter group in this context is the DMT group, which on deprotection yields a DMT cation, which can be monitored photometrically at a wavelength between 480 and 500 nm.

As used herein "β-elimination" refers to the removal of a phosphate protective group under basic conditions which involves the transfer of a hydrogen atom at the β-position of the protective group to the applied base and the release of the phosphate protective group through the cleavage of the bond between an oxygen atom of the phosphate and the protective group. The term β-elimination is further illustrated through an example, i.e. the β-elimination of a β-cyanoethyl phosphate protective group. A cyanoethyl phosphate protective group contains three carbon atoms. The first carbon atom is attached to the oxygen atom of the phosphate group and represents the α-position. The second carbon atom is attached to the first carbon atom and represents the β-position. The third carbon atom is part of the cyano group. During the removal of a β-cyanoethyl group under basic conditions a hydrogen atom is transferred from the second carbon atom, i.e. from the β-position, to the applied base, and the bond between the oxygen atom of the phosphate group and the first carbon atom is cleaved to release the β-cyanoethyl group as acrylonitrile. The removal of phosphate protective groups through β-elimination can potentially be affected in the final deprotection/cleavage step of the SPOS, commonly employed to remove the base protective groups of an oligonucleotide.

The present invention discloses novel phosphoramidite reagents for the introduction of phosphate moieties to the 3' or 5'-terminus of an oligonucleotide. The present invention also discloses a method to prepare oligonucleotides with terminal phosphate moieties by the coupling of the novel phoshoramidite reagents of the invention with terminal hydroxyl groups of oligonucleotides, followed by the subsequent removal the phosphate protective groups of the reagent.

The novel phosphoramidite reagents of the invention are comprised of two β-eliminating phosphate protective groups, wherein one of the phosphate protective groups is substituted in its α-position with a substituent that contains a nucleosidic moiety with a reporter group. The nucleosidic moiety imparts the characteristic of solidity to the reagents. Phosphoramidite reagents according to the invention, include, but are not limited to compounds having the structure illustrated by formula (1):

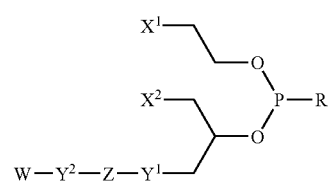

1 wherein

R is a dialkylamino group having the formula —NR'R", wherein R' and R" are independently selected from the group including, but not limited to an alkyl group having from one to about ten carbons, or wherein R' and R" together form a cyclic alkylene group having from two to up to twenty carbons which may or may not have additional alkyl substituents attached to it and which may contain up to 3 heteroatoms selected from the group consisting of N, O and S included in the cyclic alkylene group;

$X^1$ and $X^2$ are independently selected from the group including, but not limited to nitrophenyl, cyano, alkylsulfonyl, aryl, and arylsulfonyl, wherein the alkyl moiety is selected from the group including, but not limited to a branched or unbranched alkyl group having from 1 to 10 carbon atoms and the aryl moiety is selected from the group including, but not limited to a phenyl group substituted with 0 to 5 substituents, wherein said substituents are independently selected from the group including, but not limited to chlorine, fluorine, bromine, cyano and nitro.

$Y^1$ and the optional moiety $Y^2$ are independently selected from the group including, but not limited to $CH_2$, O, NH, O(CO), NH(CO), O(CO)O, O(CS)O, NH(CO)O, NH(CS)O, NH(CO)NH, (CO)O and (CO)NH;

Z is an optional spacer unit selected from the group consisting of alkylenyl and oligoethylene glycolyl and combinations thereof, which may be unsubstituted or substituted; and W is a nucleosidic moiety containing the reporter group. In one embodiment the reporter group is selected from the group including, but not limited to trityl, monomethoxy trityl and dimethoxy trityl (DMT).

In a preferred embodiment of the invention, R is a diisoproplyamino moiety, $X^1$ and $X^2$ are nitrile groups, and W is O5'-DMT-thymidin-3'-yl. In a particularly preferred embodiment of the invention, R is selected from a diisopropylamino moiety, $X^1$ and $X^2$ are nitrile groups, $Y^1$ is amido functional group —NH(CO)—, $Y^2$ is the carbamate functional group —NH(CO)O—, Z is a saturated hydrocarbon spacer of three carbons and the nucleosidic moiety W is O5'-DMT-thymidin-3'-yl. The phosphoramidite reagent according to this particularly preferred embodiment is has the following formula:

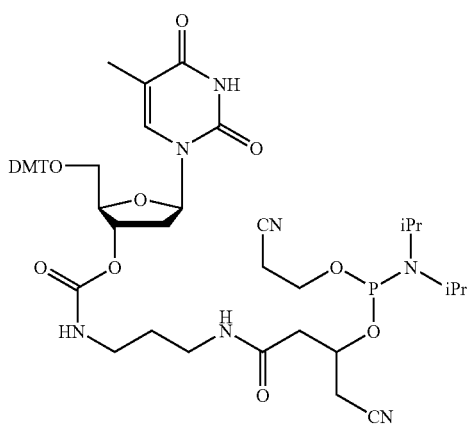

2 wherein
DMT is a 4,4'-dimethoxytrityl group; and
iPr is an isopropyl group.

The method of the invention requires that an unprotected hydroxyl group be reacted with a phosphoramidite reagent of formula (1) in the presence of an activator. There are several appropriate activators that are widely known to those skilled in the art of phosphoramidite chemistry, including, but not limited to 1H-tetrazole, 4,5-dicyanoimidazole, 5-ethylthiotetrazole, pyridinium trifluoroacetate, benzimidazolium triflate, 5-benzylthiotetrazole and other activators as described in the literature and known to those skilled in the art.

The method of the present invention is comprised of the steps of reacting an oligonucleotide with a 5'-terminal hydroxyl group, either phosphate backbone protected or not, of the formula:

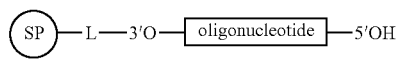

wherein
SP is the insoluble solid phase;
L is a cleavable linker that, when cleaved, gives a free hydroxyl group on the 3'-terminus of the oligonucleotide;

with a phosphoramidite reagent of formula (1) in the presence of an activator and subsequently oxidizing the product formed within the standard solid phase oligonucleotide synthesis to form a phosphorylated oligonucleotide product having the formula:

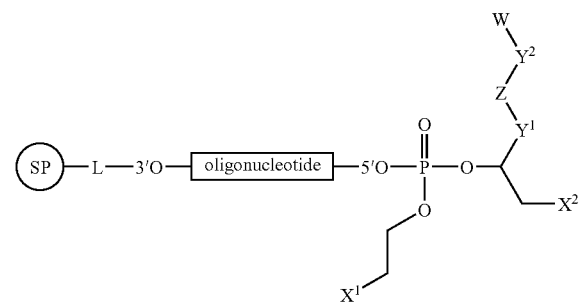

wherein
SP is the insoluble solid phase;
L is a cleavable linker which, when cleaved, gives a free hydroxyl group on the 3'-terminus of the oligonucleotide;
$X^1$ and $X^2$ are independently selected from the group including, but not limited to nitrophenyl, cyano, alkylsulfonyl, aryl, and arylsulfonyl, wherein the alkyl moiety is selected from the group including, but not limited to a branched or unbranched alkyl group having from 1 to 10 carbon atoms and the aryl moiety is selected from the group including, but not limited to a phenyl group substituted with 0 to 5 substituents, wherein said substituents are independently selected from the group including, but not limited to chlorine, fluorine, bromine, cyano and nitro.

$Y^1$ and the optional moiety $Y^2$ are independently selected from the group including, but not limited to $CH_2$, O, NH, O(CO), NH(CO), O(CO)O, O(CS)O, NH(CO)O, NH(CS)O, NH(CO)NH, (CO)O and (CO)NH;

Z is an optional spacer unit selected from the group consisting of alkylenyl and oligoethylene glycolyl and combinations thereof, which may be unsubstituted or substituted; and W is a nucleosidic moiety containing the reporter group.

The novel phosphoramidite reagents and methods of the invention can be applied with coupling yields of greater than 95%, or even greater than 99% with respect to the available hydroxyl groups.

In one embodiment of the present invention, the coupling reaction of the phosphoramidite reagent can optionally be monitored through the cleavage of the reporter group from the support-bound oligonucleotide. For example, if reagent (2) is employed, the support bound oligonucleotide can be subjected to a treatment with acid in order to remove the DMT group from the oligonucleotide. The colored DMT cation generated can then be measured quantitatively by VIS-spectroscopy. Treatment with acid can automatically and conveniently be performed in the DMT-OFF mode of commercial bench-top DNA/RNA synthesis instruments. The ratio of the quantities of the removed DMT-group from the detritylations before and after the coupling of reagent (2) directly provides the coupling efficiency of the reagent.

In the next step of the disclosed method, both phosphate protective groups of the reagent are removed under basic conditions simultaneously with the removal of the base protective groups of the oligonucleotide. The removal of the phosphate protective groups of the reagent is not dependent on the removal of the reporter group and can be conducted either with or without prior removal of the reporter group. The resulting 5'-phosphate oligonucleotide product produced in this step has the following formula:

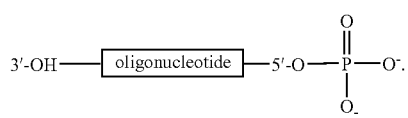

Oligonucleotides with a terminal 3'-phosphate moiety may be prepared in essentially the same manner as described for oligonucleotides with a terminal 5'-phosphate moiety if the oligonucleotide synthesis is conducted in the 5'→3'-direction rather than the 3'→5' direction as described above. Synthesis in the 3'→5'-direction results in terminal 5'-hydroxyl groups, whereas synthesis in the 5'→3' direction results in terminal 5'-hydroxyl groups. Both types of terminal hydroxyl groups can be converted into phosphate monoesters using the reagents and methods of the present invention.

The cleaved and fully deprotected oligonucleotide containing a terminal phosphate moiety may be recovered and isolated by a variety of known techniques including, but not limited to desalting, gel electrophoresis, anion exchange high pressure liquid chromatography (HPLC), reversed phase HPLC, or any other common method known to those skilled in the art for the recovery and isolation of synthetic oligonucleotides after their deprotection.

The present invention is further described by way of specific examples as discussed and enclosed hereafter. The examples are offered for illustrative purposes only and are not intended to limit the invention in any manner.

The synthesis of the phosphoramidite reagent (8) as displayed in Scheme 2 is described in Example 1. Briefly, compound (8) was synthesized from the DMT-protected aminolinker (4) and the commercially available chiral nitrile-ester (5). Aminolinker (4) was prepared from 6-amino-1-hexanol (3) in three steps according to Scheme 1 as described by Woo et al., U.S. Pat. No. 5,552,471, which is specifically incorporated herein by reference in its entirety.

Scheme 1

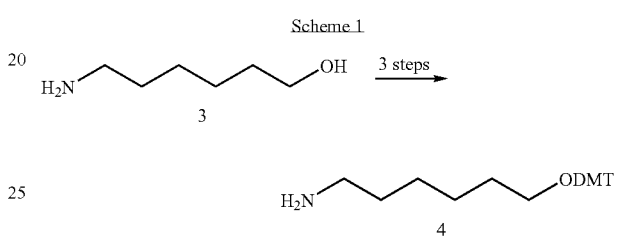

With reference to Scheme 2, saponification of the ester group of compound (5) was accomplished by treatment with aqueous sodium hydroxide solution. After neutralization with phosphate buffer the crude acid (6) was coupled with aminolinker (4) in aqueous solution by treatment with 1-(3-dimethylaminopropyl)-3-ethylcarbodiimide hydrochloride (EDC) and 1-hydroxybenzotriazole hydrate (HOBt) following a literature procedure described by Nozaki (1997) Chem. Lett. 1-2, which is specifically incorporated herein by reference in its entirety. The resulting alcohol (7) was converted into the phosphoramidite reagent (8) by treatment with chloro-(2-cyanoethyl) diisopropylaminophosphane and N,N-diisopropylethylamine (DIPEA).

Scheme 2

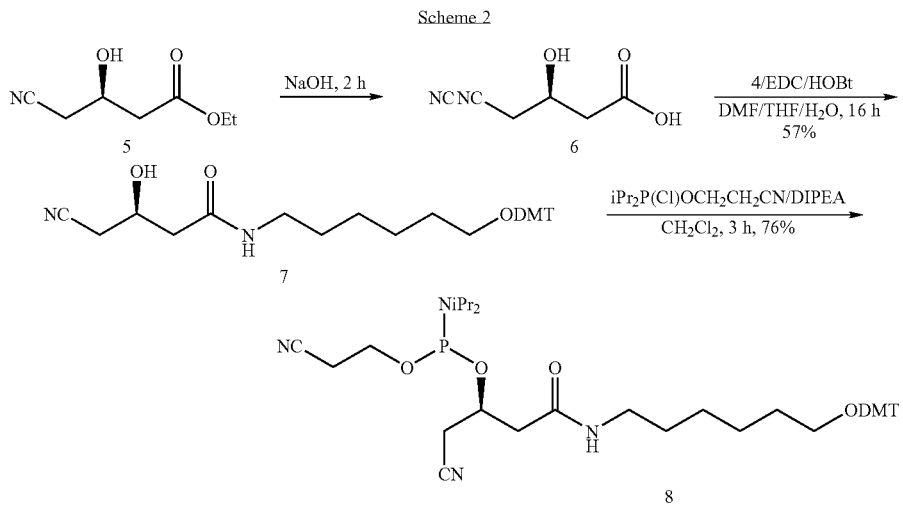

Example 2 describes the synthesis of the 5'-phosphate oligonucleotide d(T$_{10}$) (9) (SEQ ID NO: 1) according to the method of this invention using phosphoramidite reagent (8).

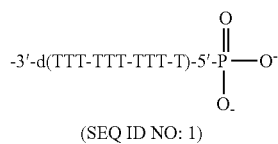

(SEQ ID NO: 1)

As described in Example 2, the oligonucleotide synthesis was performed on a 1 μmol scale using the standard DNA oligonucleotide synthesis protocol of the DNA/RNA synthesizer in the DMT-OFF mode. Phosphoramidite reagent (8) was employed as 0.1 M solution in acetonitrile in the last coupling cycle. 4,5-Dicyanoimidazole was employed as the activator for the coupling reaction as a 0.25 M solution in acetonitrile. The oligonucleotide was cleaved from the support by treatment with concentrated ammonia at room temperature for 1 hour followed by removal of the phosphate protective groups at 55° C. for 8 hours. Analysis of the product by anion-exchange HPLC demonstrated the formation of one major product in 85.7% purity. MALDI-TOF mass spectrometry confirmed the expected structure of oligodeoxynucleotide (9) (SEQ ID NO: 1).

Example 3 describes the preparation of the novel phosphoramidite reagent (2) for the conversion of terminal hydroxyl groups of oligonucleotides into phosphate monoesters. In the synthesis of the phosphoramidite reagent (2), the 3'-hydroxyl group of O5'-DMT-thymidine (10) was functionalized in three steps, as illustrated in Scheme 3. In the first step, the thymidine derivative (10) was converted into the 4-nitrophenyl-carbonate (11) by treatment with 4-nitrophenyl chloroformate in pyridine. A similar reaction to prepare compound (11) was described by Li et al. (2000) Tetrahedron Lett. 41:4323-4327, which is incorporated herein by reference in its entirety. The carbonate (11) was then added to a mixture of 1,3-diaminopropane and triethylamine to generate the carbamate (12). The condensation of (12) with the chiral acid (6) was accomplished as described in Example 1. The resulting alcohol (13) was converted into the phosphoramidite reagent (2) by treatment with chloro-(2-cyanoethyl) diisopropylaminophosphane and N,N-diisopropylethylamine (DIPEA). Phosphoramidite reagent (2) was obtained as a powder. It is a solid compound that can be easily manipulated and weighed into bottles in small portions. It dissolves readily in acetonitrile, the most common solvent of phosphoramidite couplings, and its dissolution can be easily monitored by visual inspection. This property of reagent (2) is particularly valuable as it avoids the tedious handling of very viscous liquids which is a common feature of most of the corresponding reagents of the prior art.

Scheme 3

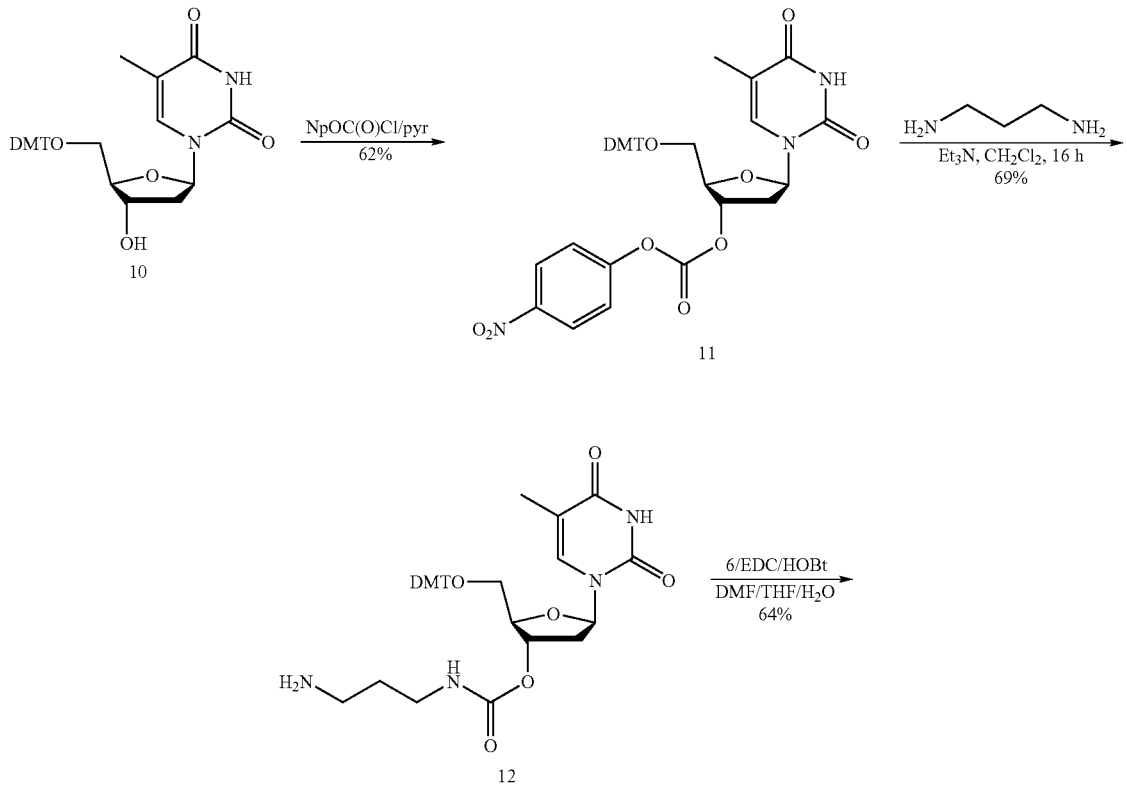

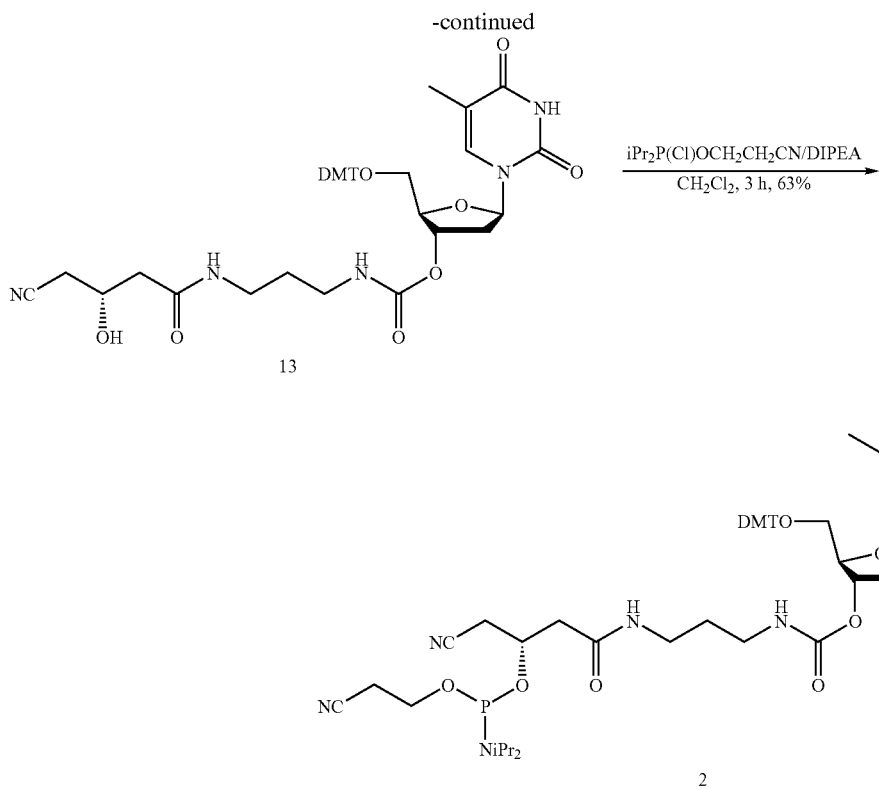

Example 4 illustrates the usefulness of the novel phosphoramidite reagent (2) by employing it in the synthesis of the 5'-phosphate oligonucleotide d(T$_{10}$) (9) (SEQ ID NO: 1). The oligonucleotide synthesis was performed on 1 μmol scale using the standard DNA oligonucleotide synthesis protocol of the DNA/RNA synthesizer in the DMT-OFF mode. Phosphoramidite reagent (2) was added as a 0.1 M solution in acetonitrile in the last coupling cycle. The oligonucleotide was cleaved from the support by treatment with concentrated ammonia at room temperature for 1 hour and the phosphate protective groups were removed at 55° C. overnight. Analysis of the product by anion-exchange HPLC demonstrated the formation of one major product with 90.8% purity. The molecular weight of the product as measured by MALDI-TOF mass spectrometry confirmed the expected structure of oligodeoxynucleotide (9). In Example 5, the efficiency for the final coupling of phosphoramidite reagent (2) was determined by measuring the quantity of the cleaved DMT-group from the detritylation reactions prior to and after the coupling of the reagent (2). The determined coupling efficiency was 97.8%.

Example 6 demonstrates the usefulness of the phosphoramidite reagent (2) in the synthesis of two 5'-phosphate base-complementary 17-mer oligodeoxynucleotides containing all 4 natural nucleobases, i.e. 3'-d(AAC TCC GAG CGA CTC TC)-5' (14) (SEQ ID NO:2) and 3'-d(GAG AGT CGC TCG GAG TT)-5' (15) (SEQ ID NO:3). The oligonucleotide synthesis was performed on 1 μmol scale using the standard DNA oligonucleotide synthesis protocol of the DNA/RNA synthesizer in the DMT-OFF mode. Phosphoramidite reagent (2) was added as 0.1 M solution in acetonitrile in the last coupling cycle. The oligonucleotide was cleaved from the support by treatment with concentrated ammonia at room temperature for 1 hour and deprotected in the concentrated ammonia solution at 55° C. overnight. Analysis of the products by anion-exchange HPLC and MALDI-TOF mass spectrometry demonstrated the clean formation of the desired oligonucleotides (14) and (15) (cf. Table 1 for results).

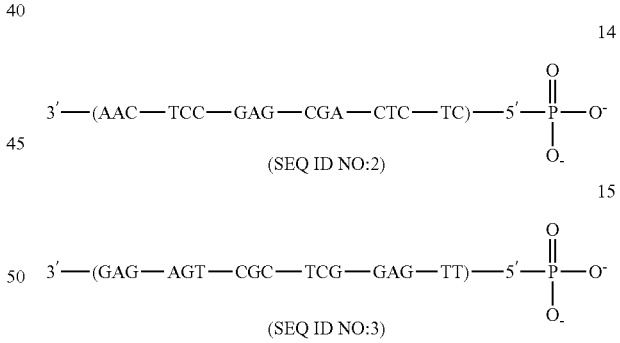

TABLE 1

Analytical data for the synthesis of oligonucleotides (14) and (15) as described in Example 6.

| Oligo- | AX-HPLC | | MALDI-MS | | |
|---|---|---|---|---|---|
| nucleotide | R$_t$ [min] | Purity [%] | Calcd | Found | OD$_{260}$ |
| (14) | 9.93 | 83.1 | 5192.3 | 5188.7 | 125.7 |
| (15) | 9.63 | 67.6 | 5343.9 | 5328.8 | 116.4 |

Example 7 provides evidence of the full compatibility of the phosphoramidite reagent (2) with common deprotection conditions in the state-of-the-art oligonucleotide synthesis. The 5'-phosphate oligonucleotide d($T_{10}$) (9) was prepared using reagent (2) according to the procedure described in Example 4, except for the cleavage from the support and the removal of the phosphate protective groups. Subsequent to the complete assembly of the oligonucleotide on the CPG support, portions of the CPG were subjected to four different deprotection conditions: concentrated ammonia at room temperature for 2 hours; concentrated ammonia/40% aq. methyl amine (1:1, v/v, referred to as AMA) at room temperature for 90 minutes; concentrated ammonia for 2 hours at 55° C.; and AMA for 10 minutes at 55° C. Additionally, the deprotection of the fifth sample was performed with concentrated ammonia at room temperature for 30 minutes in order to obtain a reference sample wherein the phosphate protective groups are incompletely removed. The oligonucleotide products from all experiments were analyzed by anion-exchange HPLC and MALDI-TOF mass spectrometry. The results are set forth in Table 2 and the structures of the observed side-products (16) and (17) are depicted below.

sufficient under the conditions of Table 2. Ammonia at room temperature removed most of the thymidine-modified cyanoethyl groups. However, it is apparent that an appreciable amount of unmodified cyanoethyl protective groups, which appears to coelute with fully deprotected oligonucleotide, are left intact. This seems to point to the conclusion that the thymidine-modified cyanoethyl group is eliminated preferentially over the unmodified cyanoethyl group. The data also suggest that the reagent (2) has characteristics with respect to the removal of the phosphate protective groups that are similar to other commercial phosphoramidite reagents for the introduction of terminal phosphate moieties because the limiting factor of the deprotection rate for reagent (2), the unmodified cyanoethyl group, is a common feature of these reagents.

The complete deprotection of the phosphate protective groups of reagent (2) within 2 hours in conc. ammonia at 55° C. demonstrates that the application of (2) is fully compatible with the standard set of base protective groups, i.e. the benzoyl protective group for adenine- and cytosine-moieties, and the isobutyryl protective group for guanine-moi-

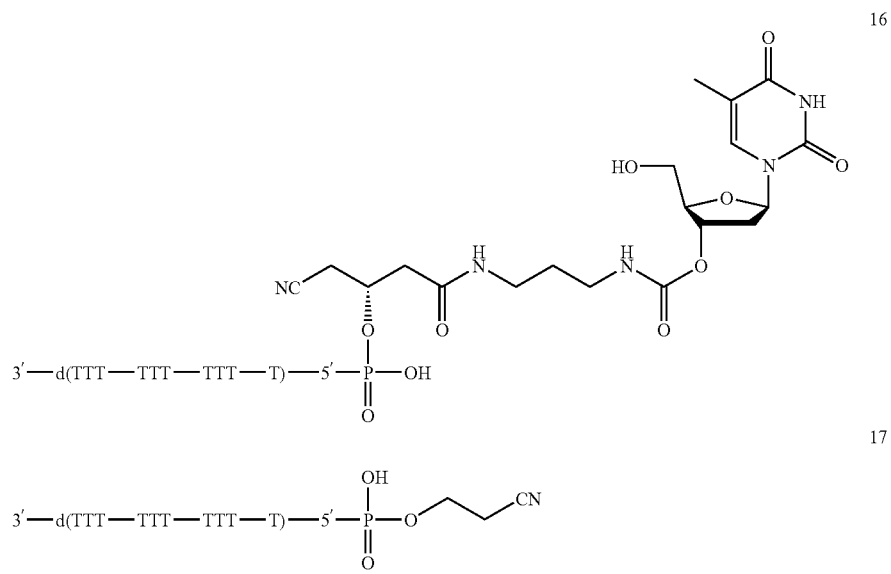

TABLE 2

Analytical results of the deprotection study described in Example 7

| # | Cleavage Conditions | Structures | AX-HPLC $R_t$ [min] | Area [%] | MALDI-MS Found | Ratio |
|---|---|---|---|---|---|---|
| 1 | NH$_4$OH, 30 min, r.t. | (16) | 16.75 | 13.5 | 3504.7 | 1:1 |
|   |                        | (9)/(17) | 17.69 | 81.9 | 3067.2/3120.7 |   |
| 2 | NH$_4$OH, 2 h, r.t.    | (16) | 16.80 | 11.6 | 3504.4 | 2:3 |
|   |                        | (9)/(17) | 17.79 | 70.4 | 3066.8/3120.3 |   |
| 3 | NH$_4$OH, 2 h, 55° C.  | (9) | 16.32 | 94.4 | 3064.1 | ./. |
| 4 | AMA, 90 min, r.t.      | (16) | 16.79 | 6.1 | 3505.5 | 7:1 |
|   |                        | (9)/(17) | 17.73 | 90.0 | 3067.8/3121.7 |   |
| 5 | AMA, 10 min 55° C.     | (16) | 16.84 | 5.7 | 3504.5 | 7:1 |
|   |                        | (9)/(17) | 17.66 | 89.0 | 3066.6/3120.7 |   |

MALDI-MS calcd: 3059.9 for (9); 3495.4 for (16); 3113.0 for (17)

The results indicate that ammonia treatment at 55° C. for 2 hours is required to completely cleave the phosphate protective groups. Application of the AMA reagent is not eties, which is conveniently deprotected within 8 hours in conc. ammonia at 55° C. The result also demonstrates full compatibility of reagent (2) with a modified set of base protective groups consisting of the benzoyl protective group for adenine- and cytosine-moieties, and the N,N-dimethylformamidine protective group for guanine-moieties, which can be completely removed from synthetic oligonucleotides within 2 hours in conc. ammonia at 55° C.

In conclusion, the novel phosphoramidite reagents of the invention for the synthesis of oligonucleotides with terminal phosphate moieties fulfill the complete set of desired criteria for such reagents in that A) they contain a reporter group that can be utilized to monitor the coupling efficiency of the reagents;

B) they contain two β-eliminating phosphate protective groups that are cleaved under basic conditions through a mechanism that does not involve an attack of a cleaving reagent at the phosphorus atom of the phosphate moiety;

C) they do not require additional chemical steps or manipulations in the course of the preparation of oligonucleotides with terminal phosphate moieties, because both phosphate protective groups of the reagents are removed simultaneously with the base protective groups of the oligonucleotide during its deprotection; and D) they are solid compounds that readily dissolve in the solvent of the coupling reaction, i.e. in acetonitrile, and they can be easily handled and weighed into bottles in small portions, and their dissolution in a solvent can be easily monitored by visual inspection.

The novel phosphoramidite reagents of the invention are therefore superior to the reagents of the prior art, because they combine all the listed desired features, a need that is unmet so far by the commercialized reagents and the reagents of the scientific literature.

Note, that throughout this application various citations are provided. Each citation is specifically incorporated herein by reference in its entirety.

EXAMPLES

Example 1

Synthesis of Phosphoramidite Reagent (8)

Synthesis of alcohol (7)

Ethyl (R)-4-cyano-3-hydroxybutanoate (Synthon Chiragenics Corporation, N.J., USA) (5) (1.00 g, 6.36 mmol) was weighed into a 100 mL round bottomed flask with a magnetic stir bar. The ester was dissolved in 1 M aqueous NaOH (15 mL, 15 mmol) and allowed to stir for 2 hours, after which TLC analysis (EtOAc/hexanes 60:40, v/v, permanganate visualization) revealed that the hydrolysis to compound (6) was complete. 1.5 M aqueous $NaH_2PO_4$ solution (15 mL) was then added to the reaction mixture and the pH was determined to be 7.0. The pH of the solution was adjusted to 5.5-6.0 by dropwise addition of HCl (conc. HCl/water 1:10, v/v). HOBt-$H_2O$ (100 mg, 0.65 mmol) was added to the reaction mixture, which was then diluted with DMF (30 mL). In a 20 mL scintillation vial, aminolinker (4) (2.50 g, 5.96 mmol) was dissolved in THF (15 mL) and added, at once, to the reaction mixture. The pH was again adjusted to 5.5-6.0 with HCl (conc. HCl/water 1:10, v/v). EDC (2.44 g, 12.73 mmol) was added and the reaction mixture was stirred overnight. TLC analysis (hexanes/EtOAc/EtOH 50:45:5, v/v/v) revealed that the reaction was complete. The reaction mixture was diluted with water (150 mL) and extracted with EtOAc (3×50 mL). The organic phase was dried over $Na_2SO_4$, filtered and the solvent removed to give a yellow oil, which was purified via flash chromatography eluting with hexanes/EtOAc/EtOH 50:45:5 (v/v/v) to provide 1.80 g (57%) of alcohol (7) as clear, colorless oil. $R_f$ 0.25 (hexanes/EtOAc/EtOH 50:45:5 [v/v/v]). $^1$H-NMR ($CD_3CN$, 300 MHz): δ 7.44 (d, J=6.6 Hz, 2H); 7.39-7.24 (m, 7H) 6.88 (d, J=9.0 Hz, 4H); 6.59 (s, 1H); 4.44-4.38 (m, 1H); 4.22-4.15 (m, 1H); 3.78 (S 6H); 3.13 (q, J=6.4 Hz, 2H); 3.01 (t, J=6.4 Hz. 2H); 2.62 (dd, J=17.0, 5.0 Hz, 1H); 2.53 (dd, J=17.0, 6.2 Hz, 1H); 2.35 (t, J=2.3 Hz, 2H); 1.65-1.20 (m, 8H). $^{13}$C-NMR ($CD_3CN$, 75 MHz): δ 171.0; 159.0; 146.2; 137.1; 130.4; 128.5; 128.2; 127.1; 118.5; 117.8; 113.4; 86.0; 65.1; 63.5; 55.4; 41.3; 39.3; 30.1; 29.5; 26.9; 26.2; 25.4.

Synthesis of the Phosphoramidite Reagent (8)

Alcohol (7) (1.44 g, 2.71 mmol) was weighed into a 100 mL round bottom flask with a magnetic stir bar. The flask was septum sealed, flushed with argon and charged with $CH_2Cl_2$ (15 mL) and DIPEA (2.5 mL, 14.35 mmol). Chloro-(2-cyanoethyl) diisopropylaminophosphane (0.67 g, 2.83 mmol) was weighed in a 1 mL syringe and added dropwise to the stirring reaction mixture. The reaction was allowed to stir for 3 hours. The reaction mixture was then diluted with $CH_2Cl_2$ (100 mL) and washed with 10% aq. $Na_2CO_3$ (2×100 mL) and brine (100 mL). The organic phase was dried over $Na_2SO_4$, filtered, and the solvent was removed. The resultant oil was purified via flash chromatography eluting with EtOAc/hexanes 60:40 (v/v) to give 1.50 g (76%) of amidite (8) as clear, colorless oil. $R_f$ 0.75 hexanes/EtOAc/EtOH 50:45:5 [v/v/v]). $^1$H-NMR ($CD_3CN$, 300 MHz): δ 7.44-7.20 (m, 9H), 6.88 (d, J=9 Hz, 4H); 6.53-6.48 (m, 1H); 4.50-4.39 (m, 1H); 3.78 (s, 6H); 3.70-3.50 (m, 2H); 3.20-3.05 (m, 2H); 3.01 (t,J=6.4 Hz, 2H); 2.80-2.60 (m, 4H); 2.60-2.37 (m, 2H); 1.65-1.53 (m, 2H); 1.50-1.15 (m, 20H). $^{13}$C-NMR ($CD_3CN$, 75 MHz): δ 169.0; 159.0; 146.1; 137.1; 130.4; 128.5; 128.2; 127.1; 118.1; 117.8; 113.4; 86.0; 67.6; 67.4; 63.5; 58.8; 58.5; 55.4; 43.7; 43.6; 43.5; 43.4; 42.0; 39.4; 30.1; 29.6; 26.9; 26.2; 25.2; 24.4; 24.3; 24.2; 20.5; 20.4. $^{31}$P-NMR ($CD_3CN$, 121.5 MHz): δ 150.3; 150.2.

Example 2

Use of Phosphoramidite Reagent (8) in the Synthesis of the 5'-phosphorylated Oligonucleotide $dT_{10}$ (9) (SEQ ID NO: 1)

The oligodeoxynucleotide (9) was synthesized using an ABI Expedite (Model 8909) DNA/RNA synthesizer. The synthesis was performed according to the manufacturer's recommendations in DMT-OFF mode employing commercial synthesis reagents. The phosphoramidite reagent (8) was added as a 0.1 M solution in acetonitrile in the last coupling cycle. The cleavage of the oligonucleotide from the support was accomplished by treatment with conc. ammonia (1 mL) at room temperature for 1 hour. The removal of the phosphate protecting groups was conducted through heating of the resulting ammonia solution of the crude oligonucleotide at 55 ° C. for 8 hours. The characterization of the product was performed by MALDI-TOF mass spectrometry: calcd 3059.9; found 3057.8. The crude oligonucleotide was analyzed by anion-exchange HPLC on a Dionex DNAPac PA100 column (4×250 mm) eluting with a linear gradient from 10% to 46% buffer B in 22.00 minutes at 85° C. with a flow rate of 1.5 mL/min, detection at λ=260 nm, buffer A=25 mM Trizma hydrochloride/1 mM EDTA/10% $CH_3CN$, pH 7.5, buffer B=25 mM Trizma hydrochloride/1 mM EDTA/10% $CH_3CN$/1 M NaCl, pH 7.5. The purity of oligonucleotide (9) was determined as 85.7% ($R_t$=16.57 minutes). The obtained quantity of oligonucleotide (9) was 73.4 $OD_{260}$.

Example 3

Synthesis of Phosphoramidite Reagent (2)

Synthesis of Amine (12)

O-5'-DMT-Thymidine (10) (5.02 g, 9.22 mmol) was weighed into a 250 mL three-neck round bottom flask. The nucleoside was coevaporated with pyridine (2×20 mL). The flask was fitted with a dropping funnel and a magnetic stir bar and the apparatus was septum sealed and flushed with argon. The flask was charged with pyridine (25 mL) and set to stir. 4-Nitrophenyl chloroformate (1.95 g, 9.68 mmol) was dissolved in $CH_2Cl_2$ (25 mL) and transferred to the dropping funnel. The flask was cooled to 0° C. and the nitrophenyl chloroformate solution was added dropwise over 30 minutes. The reaction mixture was stirred overnight at room temperature. The reaction mixture was concentrated and the remainder was redissolved in $CH_2Cl_2$ (20 mL). This solution was added slowly to stirring ether (150 mL). The resulting precipitate was filtered off and discarded. The filtrate was poured into stirring hexanes (500 mL) to give a colorless precipitate that was filtered and dried to provide 4.35 g (62%) of compound (11) as a colorless powder. A portion of the 4-nitrophenyl carbonate (11) (4.15 g, 5.85 mmol) was dissolved in $CH_2Cl_2$ (15 mL) for use in the next step.

1,3-Diaminopropane (2.16 g, 29.3 mmol) was placed in a 250 mL round bottom flask containing a stir bar. The flask was fitted with a septum, purged with argon and was then charged with triethylamine (4.1 mL, 29.3 mmol) and $CH_2Cl_2$ (50 mL) and cooled to 0° C. The 4-nitrophenyl carbonate solution was added dropwise, via syringe, to the stirring 1,3-diaminopropane solution. The reaction was stirred overnight at room temperature. The reaction mixture was diluted with $CH_2Cl_2$ (100 mL) and washed with aq. satd. $NaHCO_3$ solution (5×100 mL) and brine (100 mL). The organic phase was dried over $Na_2SO_4$, filtered and the solvent removed to provide a yellow foam, which was purified via flash chromatography eluting with $CH_2Cl_2$/EtOH/$Et_3N$ 80:15:5 (v/v/v) to give 2.60 g (69%) of amine (12) as a colorless amorphous solid. $R_f$ 0.08 ($CH_2Cl_2$/EtOH/$Et_3N$ 80:15:5, v/v/v). $^1$H-NMR ($CD_3CN$, 300 MHz): δ 7.50-7.41 (m, 3H); 7.38-7.25 (m, 7H); 6.90 (d, J=8.8 Hz, 4H); 6.26 (dd, J=5.9, 2.6 Hz, 1H); 6.10-6.04 (m, 1H); 5.35-5.29 (m, 1H); 4.08 (d, J=2.6, 1H); 3.78 (s, 6H); 3.40 (dd, J=10.5 Hz, 3.4, 1H); 3.31 (dd, J=10.5, 2.9 Hz, 1H); 3.16 (q, J=6.5 Hz, 2H); 2.65 (t, J=6.7 Hz, 2H); 2.50-2.30 (m, 2H); 1.57 (q, J=6.7 Hz, 2H); 1.42 (s, 3H). $^{13}$C-NMR ($CD_3CN$, 75 MHz): δ 164.0; 159.0; 156.1; 150.8; 145.0; 136.0; 135.8; 130.3; 128.3; 128.2; 127.3; 113.4; 110.9; 86.9; 84.4; 84.2; 75.2; 64.0; 55.2; 38.7; 38.3; 37.6; 32.2; 11.4.

Synthesis of Alcohol (13)

Ethyl (R)-4-cyano-3-hydroxybutanoate (5) (0.702 g, 4.47 mmol) was weighed into a 100 mL round bottomed flask equipped with a magnetic stir bar. The ester was dissolved in 1 M aq. NaOH (9 mL, 9 mmol) and allowed to stir for 2 hours. TLC analysis (EtOAc/hexanes, 60:40, v/v, permanganate visualization) revealed that the hydrolysis was complete. 1.5 M aq. $NaH_2PO_4$ (9 mL) was added to the reaction mixture and the pH was determined to be 7.0. The pH of the solution was adjusted to 5.7 with conc. HCl. HOBt·$H_2O$ (70 mg, 0.46 mmol) was added to the reaction mixture, which was then diluted with DMF (9 mL). Amine (12) (1.35 g, 2.09 mmol) was weighed into a 20 mL scintillation vial and added, at once, to the reaction mixture. The scintillation vial was rinsed with THF (4 mL), which was added to the reaction mixture. The reaction mixture was again pH adjusted to pH 6.0 with HCl (conc. HCl/water 1:10, v/v). EDC (0.801 g, 4.18 mmol) was added and the reaction mixture was stirred overnight. TLC-analysis (EtOAc/hexanes/EtOH 70:25:5, v/v/v) revealed that the reaction was complete. The reaction mixture was diluted with water (100 mL) and extracted with EtOAc (3×50 mL). The organic phase was dried with $Na_2SO_4$, filtered and the solvent removed. The crude product was purified via flash chromatography eluting with EtOAc/hexanes/acetonitrile 70:25:5 (v/v/v) to provide 1.01 g (64%) of compound (13) as a colorless foam. $R_f$ 0.43 (EtOAc/hexanes/EtOH 70:25:5, v/v/v) $^1$H-NMR ($CD_3CN$, 300 MHz): δ 9.09 (bs, 1H); 7.50-7.40 (m, 3H); 7.38-7.23 (m, 7H); 6.90 (d, J=8.8 Hz, 4H); 6.68-6.61 (m, 1H.); 6.27 (dd, J=6.2, 2.3 Hz, 1H); 5.86 (t, J=6.2 Hz, 1H); 5.34-5.28 (m, 1H); 4.19 (qui., J=6.5 Hz, 1H); 4.12-4.08 (m, 1H); 3.78 (s, 6H); 3.41 (dd, J=10.5, 3.4 Hz, 1H); 3.32 (dd, J=10.5, 2.9 Hz, 1H); 3.20 (qui., J=6.4 Hz, 2H); 3.11 (dt, J=7.2, 6.4 Hz, 2H); 2.63 (dd, J=16.8, 5.0 Hz, 1H); 2.53 (dd, J=16.8, 6.2 Hz, 1H); 2.45-2.30 (m, 4H); 2.18 (s, 1H); 1.61 (qui., J=6.4 Hz, 2H); 1.43 (s, 3H). $^{13}$C-NMR ($CD_3CN$, 75 MHz): δ 171.1; 163.8; 159.0; 156.0; 150.7; 145.1; 135.8; 135.7; 130.3; 128.3; 128.2; 127.3; 118.3; 113.4; 110.8; 86.9; 84.4; 84.2; 75.3; 64.8; 64.0; 55.2; 41.5; 37.8; 37.5; 36.1; 29.5; 25.2; 11.4.

Synthesis of the Phosphoramidite Reagent (2)

Alcohol (13) (0.950 g, 1.26 mmol) was weighed into a 100 mL round bottom flask equipped with a magnetic stir bar. The flask was septum sealed, flushed with argon and charged with $CH_2Cl_2$ (15 mL) and DIPEA (2.2 mL, 12.6 mmol). Chloro-(2-cyanoethyl) diisopropylaminophosphane (0.312 g, 1.32 mmol) was weighed into a 1 mL syringe and added dropwise to the stirring reaction mixture. The reaction was stirred for 3 hours, after which it was concentrated and redissolved in EtOAc (100 mL) and washed with 10% aq. $Na_2CO_3$ (2×50 mL) and brine (50 mL). The organic phase was dried over $Na_2SO_4$, filtered, and the solvent was removed. The resultant foam was purified via flash chromatography eluting with EtOAc/$CH_2Cl_2$/acetonitrile 70:23:7 (v/v/v) to give 0.758 g (63%) of compound (2) as a colorless foam. $R_f$ 0.25 (EtOAc/$CH_2Cl_2$/acetonitrile 70:23:7, v/v/v) $^1$H-NMR ($CD_3CN$, 300 MHz): δ 9.11 (bs, 1H); 7.55-7.42 (m, 3H); 7.40-7.25 (m, 7H); 6.90 (d, J=9.1 Hz, 4H); 6.67-6.60 (m, 1H); 6.27 (dd, J=6.3, 2.0 Hz, 1H); 5.90 (t,J=6.2 Hz, 1H); 5.35-5.27 (m, 1H); 4.50-4.38 (m, 1H); 4.11-4.07 (m, 1H); 3.90-3.69 (m, 8H); 3.67-3.50 (m, 2H); 3.40 (dd, J=10.4, 3.7 Hz, 1H); 3.31 (dd, J=10.4, 3.1 Hz, 1H); 3.27-3.05 (m, 4H); 2.80-2.30 (m, 8H); 1.60 (qui., J=6.3 Hz, 2H); 1.44 (s, 3H) 1.25-1.15 (m, 12H). $^{13}$C-NMR ($CD_3CN$, 75 MHz): δ 169.6; 164.0; 159.3; 156.2; 151.0; 145.3; 136.0; 135.9; 130.5; 128.5; 128.4; 127.5; 119.2; 117.8; 113.6; 111.1; 87.1; 84.6; 84.4; 75.4; 67.9; 67.6; 67.5; 67.3; 64.3; 59.0; 58.8; 55.4; 43.7; 43.6; 43.5; 42.3; 42.1; 38.2; 37.8; 36.5; 29.9; 25.2; 24.4; 24.3; 20.4; 11.7. $^{31}$P-NMR ($CD_3CN$, 121.5 MHz): δ 150.2; 150.1.

Example 4

Application of Phosphoramidite Reagent (2) in the Synthesis of the 5'-phosphorylated Oligonucleotide $dT_{10}$ (9) (SEQ ID NO: 1)

The oligodeoxynucleotide (9) was synthesized using an ABI Expedite (Model 8909) DNA synthesizer. The synthesis was performed according to the manufacturer's recommendations in DMT-OFF mode employing commercial synthesis reagents. The phosphoramidite reagent (2) was added as 0.1 M solution in acetonitrile in the last coupling cycle.

Cleavage of the oligonucleotide from the support was accomplished by treatment with conc. ammonia (1 mL) at room temperature for 1 hour. The removal of the phosphate protecting groups was conducted through heating of the resulting ammonia solution of the crude oligonucleotide at 55° C. over night (16 hours). Characterization of the product was performed by MALDI-TOF mass spectrometry: calcd 3059.9; found 3065.4. The crude oligonucleotide was analyzed by anion-exchange HPLC on a Dionex DNAPac PA100 column (4×250 mm) eluting with a linear gradient from 10% to 46% buffer B in 22.00 minutes at 85° C. with a flow rate of 1.5 mL/min, detection at $\lambda=260$ nm, buffer A=25 mM Trizma hydrochloride/1 mM EDTA/10% $CH_3CN$, pH 7.5, buffer B=25 mM Trizma hydrochloride/1 mM EDTA/10% $CH_3CN$/1M NaCl, pH 7.5. The purity of oligonucleotide (9) was determined as 90.8% ($R_f$=15.62 min.). The obtained quantity of oligonucleotide (9) was 79.1 $OD_{260}$.

Example 5

Determination of the Coupling Efficiency for Phosphoramidite Reagent (2) in the Synthesis of the 5'-phosphorylated Oligonucleotide $dT_{10}$ (9) (SEQ ID NO: 1)

The oligodeoxynucleotide (9) was synthesized on a 1 µmol scale using an ABI 391 DNA Synthesizer. The synthesis was performed according to the manufacturer's recommendations employing commercial synthesis reagents. The column effluents from the detritylation step with Deblock Solution (3% TCA in DCM) and from the following wash step (acetonitrile) were collected and combined in a 25 mL graduated flask for the detritylations before and after the coupling of the phosphoramidite reagent (2). The graduated flasks were filled to a total of 25.0 mL with Deblock Solution and the extinctions of the solutions of the orange dimethoxytrityl cation were measured at 480 nm with a Beckman Coulter DU 800 spectrophotometer. Extinction values of 0.7910 and 0.7734, respectively, were obtained, resulting in a coupling efficiency of phosphoramidite reagent (2) of 97.8%.

Example 6

Application of the Phosphoramidite Reagent (2) in the Synthesis of the 5'-phosphorylated Hetero Sequences (14) (SEQ ID NO:2) and (15) (SEQ ID NO:3)

The oligodeoxynucleotides (14) and (15) were synthesized using an ABI Expedite (Model 8909) DNA synthesizer. The syntheses were performed according to the manufacturer's recommendations in DMT-OFF mode employing commercial synthesis reagents. Phosphoramidite reagent (2) was added as 0.1 M solution in acetonitrile in the last coupling cycle of each synthesis, respectively. The cleavage of the oligonucleotides from the support was accomplished by treatment of each support sample with conc. ammonia (1 mL, each) at room temperature for 1 hour. The deprotection of the oligonucleotides and the concomitant removal of the phosphate protective groups was conducted by heating of the ammonia solutions of the oligonucleotides at 55° C. overnight (16 hours). The analysis of the oligonucleotide products was performed by MALDI-TOF mass spectrometry and anion-exchange HPLC on a Dionex DNAPac PA100 column (4×250 mm) eluting with a linear gradient from 36% to 80% buffer B in 22.00 minutes at 85° C. with a flow rate of 1.5 mL/min, detection at $\lambda=260$ nm, buffer A=25 mM Trizma hydrochloride/1 mM EDTA/10% $CH_3CN$, pH 7.5, buffer B=25 mM Trizma hydrochloride/1 mM EDTA/10% $CH_3CN$/1M NaCl, pH 7.5. The results are set forth in Table 1.

Example 7

Cleavage from the Support and Removal of Phosphate Protective Groups from the CPG Bound 5'-phosphorylated Oligonucleotide $d(T_{10})$ Prepared with the Phosphoramidite Reagent (2) under Various Basic Conditions Three samples of oligodeoxynucleotide (9) (SEQ ID NO: 1) were synthesized using an ABI Expedite (Model 8909) DNA synthesizer. The syntheses were performed according to the manufacturer's recommendations in DMT-OFF mode employing commercial synthesis reagents. The phosphoramidite reagent (2) was added in each synthesis as 0.1 M solution in acetonitrile in the last coupling cycle. After the synthesis one CPG sample (#1) was treated with conc. ammonia (1 mL) for 30 minutes at room temperature. The remaining two CPG columns were opened and each CPG batch was divided evenly between two deprotection vials. Each vial was treated with a basic deprotection solution (500 µL): sample #2 and #3 with conc. ammonia; sample #4 and #5 with AMA. The samples were processed at the temperature and for the time set forth in Table 2. All samples were analyzed by MALDI-TOF mass spectrometry and anion-exchange HPLC on a Dionex DNAPac PA100 column (4×250 mm) eluting with a linear gradient from 10% to 46% buffer B in 22.00 minutes at 85° C. with a flow rate of 1.5 mL/min, detection at $\lambda=260$ nm, buffer A=25 mM Trizma hydrochloride/1 mM EDTA/10% $CH_3CN$, pH 7.5, buffer B=25 mM Trizma hydrochloride/1 mM EDTA/10% $CH_3CN$/1M NaCl, pH 7.5. The results are set forth in Table 2.

We claim:

1. A phosphoramidite reagent having the formula (2'):

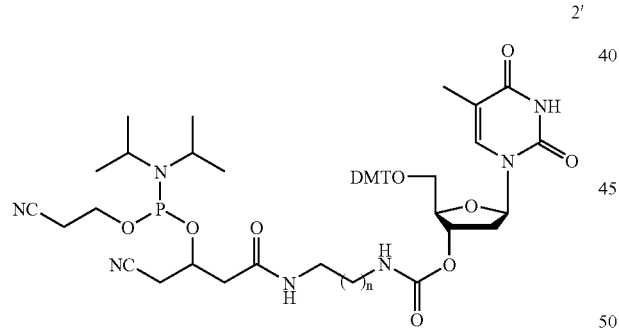

wherein n is an integer selected from 0 to 20.

* * * * *

SEQUENCE LISTING

<160> NUMBER OF SEQ ID NOS: 3

<210> SEQ ID NO 1
<211> LENGTH: 10
<212> TYPE: DNA
<213> ORGANISM: Artificial Sequence
<220> FEATURE:
<223> OTHER INFORMATION: Synthetic Nucleic Acid Ligand

```
-continued

<220> FEATURE:
<221> NAME/KEY: misc_feature
<222> LOCATION: (1)..(10)

<400> SEQUENCE: 1
tttttttttt                                                           10

<210> SEQ ID NO 2
<211> LENGTH: 17
<212> TYPE: DNA
<213> ORGANISM: Artificial Sequence
<220> FEATURE:
<223> OTHER INFORMATION: Synthetic Nucleic Acid Ligand
<220> FEATURE:
<221> NAME/KEY: misc_feature
<222> LOCATION: (1)..(17)

<400> SEQUENCE: 2
aactccgagc gactctc                                                   17

<210> SEQ ID NO 3
<211> LENGTH: 17
<212> TYPE: DNA
<213> ORGANISM: Artificial Sequence
<220> FEATURE:
<223> OTHER INFORMATION: Synthetic Nucleic Acid Ligand
<220> FEATURE:
<221> NAME/KEY: misc_feature
<222> LOCATION: (1)..(17)

<400> SEQUENCE: 3
gagagtcgct cggagtt                                                   17
```